United States Patent [19]

Beausang et al.

[11] Patent Number: 5,840,503
[45] Date of Patent: Nov. 24, 1998

[54] NUCLEAR MATRIX PROTEIN FLUID ASSAY

[75] Inventors: Lee Anne Beausang, Norfolk; Graham P. Lidgard, Wellesley; Thomas E. Miller, Franklin, all of Mass.

[73] Assignee: Matritech, Inc., Newton, Mass.

[21] Appl. No.: 444,821

[22] Filed: May 18, 1995

Related U.S. Application Data

[62] Division of Ser. No. 112,646, Aug. 26, 1993, abandoned, which is a continuation of Ser. No. 785,804, Oct. 31, 1991, abandoned.

[51] Int. Cl.⁶ ...................... G01N 33/567; G01N 33/574; G01N 33/53; C12Q 1/00
[52] U.S. Cl. .......................... 435/7.21; 435/7.2; 435/7.23; 435/7.1; 435/4
[58] Field of Search ............................... 435/7.21, 4, 7.1, 435/7.23

[56] References Cited

U.S. PATENT DOCUMENTS

| | | |
|---|---|---|
| 4,628,027 | 12/1986 | Gay . |
| 4,806,463 | 2/1989 | Goodchild et al. . |
| 4,861,581 | 8/1989 | Epstein et al. ........................... 424/1.1 |
| 4,882,268 | 11/1989 | Penman et al. ............................ 435/5 |
| 4,885,236 | 12/1989 | Penman et al. ............................ 435/6 |
| 4,937,185 | 6/1990 | Webb et al. ................................ 435/7 |
| 5,032,508 | 7/1991 | Naughton et al. ........................ 435/32 |
| 5,098,890 | 3/1992 | Gewtiz et al. . |
| 5,273,877 | 12/1993 | Fey et al. . |
| 5,686,562 | 11/1997 | Toukatly et al. . |
| 5,698,439 | 12/1997 | Toukatly et al. . |

FOREIGN PATENT DOCUMENTS

| | | |
|---|---|---|
| WO87/03910 | 7/1987 | WIPO . |
| WO 89/06697 | 7/1989 | WIPO . |
| WO91/17266 | 4/1991 | WIPO . |
| WO93/09437 | 5/1993 | WIPO . |

OTHER PUBLICATIONS

Getzenberg et al. (1990) "Tissue Specificity and Cell Death are Associated with Specific Alterations in Nuclear Matrix Proteins," Abstract published in The Journal of Urology, AUA Eighty–fifth Annual Meeting, May 13–17, 1990, 143: No. 4, Abstract No. 155.

Miller et al. (1991) "Release of Nuclear Matrix Proteins during Apoptotic Cell Death," Abstract published in J. Cell Biol., 115: No. 3, Abstract No. 1822.

Miller et al. (1992) "Detection of Nuclear Matrix Proteins in Serum from Cancer Patients," Cancer Research, 52:422–427.

Compton et al., "Identification of Novel Centromere/Kinetochore–associated Proteins Using Monoclonal Antibodies Generated Against Human Mitotic Chromosome Scaffolds"; *J. of Cell Biol.*; 112 (No. 6):1083–1097 (Mar. 1991).

Fey et al., "The Nuclear Matrix: Defining Structural and Functional Roles"; *Critical Reviews in Euk. Gene Expression*; 1(2):127–143 (1991).

Kallajoki, et al.;"A 210 kD nuclear matrix protein is a functional part of the mitotic spindle; a microinjection study using SPN monoclonal antibodies," *EMBO J.*; 10:3351–3362 (1991).

Keesee et al., "Utilization of Nuclear Matrix Proteins for Cancer Diagnosis," *Critical Reviews in Eukaryotic Gene Expression*; 6(2&3):189–214 (1996).

Lydersen et al., "Human–Specific Nuclear Protein That Associates with the Polar Region of the Mitotic Apparatus: Distribution in a Human/Hamster Hybrid Cell," *Cell*; 22:489–499 (1980).

Maekawa et al., "Identification of a Minus End–Specific Microtubule–Assoicated Protein Located at the Mitotic Poles in Cultured Mammalian Cells," *European J. of Cell Biology*; 54:255–267 (1991).

Oeller et al., "Reversible Inhibition of Tomato Fruit Senescence by Antisense RNA," *Science*; 254:437–439 (1991).

Thibodeau et al., "Monoclonal Antibody CC–3 Recognizes Phosphoproteins in Interphase and Mitotic Cells," *Experimental Cell Research*; 195:145–153 (1991).

Tousson, "Centrophilin: A Novel Mitotic Spindle Protein Involved in Microtubule Nucleation," *J. of Cell Biol.*; 112 (No. 3):427–440 (1991).

Whitfield et al., "Cloning of a Gene Encoding an Antigen Associated with the Centrosome in Drosophila," *J. of Cell Science*; 89:467–480 (1988).

News Release, "Clinical Utility of Matritech's Bladder Cancer Test Reported in August Issue of Journal of Urology," (Jul. 1996).

Kohler et al. (1975) "Continuous Culures of Fused Cells Secreting Antibody of Predefined Specificity," *Nature* 256:495–497.

Wyllie et al. (1980) "Cell Death: The Significance of Apoptosis," *International Review of Cytol.* 68:251–306.

Scopes, R.K. (1982) *Protein–Purification—Principles and Practice* Springer–Verlag Eds., New York, pp. 43–52.

(List continued on next page.)

*Primary Examiner*—Nita Minnifield
*Attorney, Agent, or Firm*—Testa, Hurwitz & Thibeault, LLP

[57] ABSTRACT

Disclosed is a method for evaluating the efficacy of a therapy associated with cell death in a patient undergoing such a therapy. The method involves providing at least two body fluid samples drawn from the patient, wherein a second sample is drawn from the patient after a first sample, and measuring the quantity per unit volume of a body-fluid soluble interior nuclear matrix protein in each of the samples. By comparing the quantity per unit volume of the body fluid-soluble interior nuclear matrix protein in the first sample with the quantity per unit volume of the body fluid-soluble interior nuclear matrix protein in the second sample, it is possible to determine whether there has been an increase or decrease of cell death in the patient during therapy.

25 Claims, 8 Drawing Sheets

OTHER PUBLICATIONS

Weeks et al. (1986) "Immunoassays Using Acridinium Esters," *Methods in Enzymology* 133:366–387.

Walker et al. (1988) "Patterns of Cell Death," *Meth. Achiev. Exp. Pathol.* 13:18–54.

Fey et al. (1988) "Nuclear Matrix Proteins Reflect Cell Type of Origin in Cultured Human Cells," *Proc. Natl. Acad. Sci. USA* 85:121–125.

Domasheno et al. (1990) "Comparison of the Spectra of Proteins Synthesized in Mouse Thymocytes After Irradiation or Hydrocortisone Treatment," *Int. J. Radiol. Biol.* 57(2):315–329.

*Genetic Eng News,* Journal Announcement, Jul.–Aug. 1990, 10(7):28.

Larrick et al. (1990) "Cytotoxic Mechanism of Tumor Necrosis Factor–α," *FASEB J.* 4:3215–3223.

|  |  | ANTIBODY COMBINATIONS | | | |
|---|---|---|---|---|---|
| SAMPLE | SAMPLE # | 302-22 / 302-18 | 302-33 / 107-7 | 302-29 / 302-18 | 302-29 / 107-7 |
| NORMAL | 1 | 0.0 | 0.0 | 0.0 | 0.0 |
| NORMAL | 2 | 0.0 | 0.0 | 0.0 | 0.0 |
| NORMAL | 3 | 0.0 | 0.0 | 0.0 | 0.0 |
| NORMAL | 4 | 0.0 | 0.0 | 0.0 | 0.0 |
| NORMAL | 5 | 0.0 | 0.0 | 0.0 | 0.0 |
| NORMAL | 6 | 0.0 | 0.0 | 0.0 | 0.0 |
| NORMAL | 7 | 0.0 | 0.0 | 0.0 | 0.0 |
| NORMAL | 8 | 0.0 | 0.0 | 0.0 | 0.0 |
| NORMAL | 9 | 0.0 | 0.0 | 0.5 | 0.0 |
| NORMAL | 10 | 0.0 | 0.7 | 1.2 | 0.0 |
| NORMAL | 11 | 0.0 | 0.0 | 0.0 | 0.0 |
| NORMAL | 12 | 0.0 | 0.0 | 0.0 | 0.2 |
| NORMAL | 13 | 0.0 | 0.7 | 0.0 | 0.3 |
| NORMAL | 14 | 0.0 | 1.3 | 0.0 | 0.6 |
| NORMAL | 15 | 0.0 | 5.3 | 0.0 | 1.7 |
| NORMAL | 16 | 0.0 | 1.4 | 0.0 | 0.4 |
| NORMAL | 17 | 0.0 | 2.2 | 0.0 | 1.0 |
| NORMAL | 18 | 0.0 | 2.0 | 0.0 | 0.0 |
| NORMAL | 19 | 0.0 | 3.0 | 0.0 | 0.4 |
| NORMAL | 20 | 0.0 | 2.3 | 0.0 | 1.3 |
| NORMAL | 21 | 0.0 | 3.9 | 0.0 | 0.6 |
| NORMAL | 22 | 0.0 | 8.2 | 0.0 | 1.3 |
| NORMAL | 23 | 0.0 | 4.0 | 0.0 | 0.8 |
| NORMAL | 24 | 0.0 | 4.3 | 0.0 | 0.7 |
| NORMAL | 25 | 0.0 | 9.1 | 0.0 | 0.6 |
| NORMAL | 26 | 0.0 | 5.9 | 0.0 | 0.2 |
| NORMAL | 27 | 0.0 | 20.6 | 0.0 | 6.0 |
| NORMAL | 28 | 0.9 | 2.2 | 0.9 | 0.7 |
| NORMAL | 29 | 1.4 | 5.0 | 0.0 | 1.0 |
| NORMAL | 30 | 1.4 | 3.5 | 1.4 | 1.2 |
| NORMAL | 31 | 1.9 | 10.1 | 3.9 | 1.0 |
| NORMAL | 32 | 2.1 | 3.3 | 0.0 | 6.3 |
| NORMAL | 33 | 2.8 | 1.5 | 0.0 | 0.0 |
| NORMAL | 34 | 4.1 | 6.9 | 6.6 | 0.8 |
| NORMAL | 35 | 4.2 | 0.0 | 5.4 | 0.0 |
| NORMAL | 36 | 11.0 | 1.2 | 5.6 | 0.0 |
| BLADDER CA | 37 | 0.0 | 0.0 | 0.0 | 0.0 |
| BLADDER CA | 38 | 36.7 | 1.6 | 0.0 | 0.0 |
| BLADDER C | 39 | 0.0 | 0.0 | 0.0 | 0.0 |
| COLON CA | 40 | 8.8 | 8.9 | 8.6 | 7.0 |
| COLON CA | 41 | 18.2 | 28.4 | 20.8 | 24.3 |
| COLON CA | 42 | 18.1 | 28.6 | 19.5 | 17.9 |
| COLON CA | 43 | 14.2 | 11.6 | 15.5 | 8.1 |
| COLON CA | 44 | 9.5 | 12.8 | 13.3 | 6.8 |
| COLON CA | 45 | 5.1 | 6.4 | 4.1 | 0.9 |
| COLON CA | 46 | 4.9 | 3.7 | 5.1 | 2.4 |

Fig. 1.1

|  |  | ANTIBODY COMBINATIONS | | | |
|---|---|---|---|---|---|
| SAMPLE | SAMPLE # | 302-22<br>302-18 | 302-33<br>107-7 | 302-29<br>302-18 | 302-29<br>107-7 |
| COLON CA | 47 | 30.8 | 28.3 | 65.3 | 27.3 |
| COLON CA | 48 | 96.2 | 17.5 | 82.4 | 20.2 |
| COLON CA | 49 | 3.3 | 4.7 | 0.0 | 0.0 |
| COLON CA | 50 | 10.1 | 11.7 | 8.3 | 10.3 |
| COLON CA | 52 | 2.4 | 5.7 | 64.7 | 0.0 |
| COLON CA | 53 | 6.7 | 5.1 | 5.5 | 0.5 |
| COLON CA | 54 | 5.1 | 6.0 | 1.3 | 1.8 |
| COLON CA | 55 | 3.9 | 13.1 | 7.1 | 2.3 |
| COLON CA | 56 | 62.4 | 9.6 | 52.4 | 5.8 |
| COLOREC CA | 57 | 14.0 | 58.2 | 15.2 | 41.3 |
| ENDOMETRIUM C | 58 | 7.6 | 10.3 | 106.0 | 6.8 |
| ENDOMETRIUM C | 59 | 2.7 | 4.7 | 1.8 | 1.9 |
| ENDOMETRIUM C | 60 | 7.9 | 9.4 | 8.2 | 7.1 |
| LUNG CA | 61 | 10.0 | 13.4 | 10.7 | 9.3 |
| LUNG CA | 62 | 9.5 | 11.9 | 11.0 | 7.9 |
| LUNG CA | 63 | 11.3 | 19.0 | 13.5 | 16.2 |
| LUNG CA | 64 | 6.5 | 16.7 | 8.5 | 7.8 |
| LUNG CA | 65 | 12.6 | 20.8 | 14.9 | 11.0 |
| OVARY CA | 66 | 14.3 | 21.1 | 17.4 | 16.9 |
| OVARY CA | 67 | 7.0 | 16.4 | 9.9 | 8.9 |
| OVARY CA | 68 | 8.9 | 11.6 | 11.5 | 8.3 |
| PROSTATE CA | 69 | 11.4 | 12.7 | 13.8 | 10.8 |
| PROSTATE CA | 70 | 2.0 | 4.9 | 2.5 | 2.8 |
| PROSTATE CA | 71 | 6.4 | 0.0 | 9.3 | 3.4 |
| PROSTATE CA | 72 | 5.4 | 15.4 | 6.3 | 7.0 |
| PROSTATE CA | 73 | 2.2 | 0.0 | 1.6 | 0.0 |

Fig. 1.2

| TISSUE TYPE | ASSAY 1* | ASSAY 2** | ASSAY 3*** |
|---|---|---|---|
| BREAST NORMAL 90-247 | NT# | 500 | 1250 |
| BREAST NORMAL 90-252 | 7574 | 2705 | 5024 |
| BREAST NORMAL 90-254 | NT | 1513 | 2789 |
| BREAST NORMAL 90-264 | NT | 0 | 1685 |
| BREAST NORMAL 90-268 | 139 | NT | 432 |
| BREAST CANCER 90-256 | 438 | NT | 2750 |
| BREAST CANCER 90-275 | 2000 | NT | 9429 |
| BREAST CANCER 90-287 | 20222 | 7333 | 8600 |
| CERVIX NORMAL 90-279 | 2500 | NT | 12571 |
| CERVICAL CANCER 90-8083 | 12666 | NT | 70680 |
| COLON NORMAL 90-253 | 1009 | NT | 1689 |
| COLON CANCER 90-250 | 1450 | NT | 4275 |
| KIDNEY NORMAL 90-259 | 4250 | NT | 4275 |
| KIDNEY CANCER 90-289 | 2407 | NT | 5796 |
| LIVER NORMAL | 2154 | 614 | 202 |
| LIVER NORMAL 90-451 | NT | 131 | 420 |
| LIVER CANCER | 2227 | 0 | 932 |
| MET LIVER 90-403 | NT | 300 | 1133 |
| LUNG NORMAL 90-248 | 4391 | NT | 6636 |
| LUNG NORMAL 90-246 | 4200 | NT | 10000 |
| LUNG NORMAL 90-107 | NT | 4166 | 388 |
| LUNG NORMAL 90-118 | NT | 650 | 1200 |
| LUNG CANCER 90-095 | NT | 5357 | 16077 |
| LUNG CANCER 90-121 | NT | >12000 | 40771 |
| OVARIAN CANCER | 8621 | 6517 | 2760 |
| OVARIAN CANCER 90-260 | 6900 | NT | 20680 |
| OVARIAN CANCER 90-291 | 2768 | NT | 5750 |
| OVARIAN CANCER 90-291 | NT | 10909 | 14454 |
| UTERINE CANCER 90-277 | 6574 | NT | 70684 |
| UTERUS NORMAL 90-295 | 6574 | NT | 41444 |
| AVERAGE NORMAL | 3447 | 1284 | 5759 |
| AVERAGE CANCER | 9442 | 7069 | 26321 |

\*   ASSAY 1 IS 107.7 SOLID PHASE AND 307.33 SOLUBLE PHASE.
\*\*  ASSAY 2 IS 107.7 SOLID PHASE AND 302.29 SOLUBLE PHASE.
\*\*\* ASSAY 3 IS 302.18 SOLID PHASE AND 302.22 SOLUBLE PHASE.
\#   NT MEANS NOT TESTED.

Fig. 2

NUCLEAR MATRIX PROTEIN FLUID ASSAY

This application is a divisional of U.S. Ser. No. 08/112, 646, filed Aug. 26, 1993, now abandoned, which is a continuation of U.S. Ser. No. 07/785,804, filed Oct. 31, 1991, now abandoned.

REFERENCE TO RELATED APPLICATIONS

Related applications include: U.S. Ser. No. 08/456,620, filed Jun. 1, 1995, which is a continuation of U.S. Ser. No. 08/112,646, filed Aug. 26, 1993, now abandoned, which is a continuation of U.S. Ser. No. 07/785,804, filed Oct. 31, 1991, now abandoned; U.S. Ser. No. 08/443,630, filed May 18, 1995, a divisional of U.S. Ser. No. 08/112,646, filed Aug. 26, 1993, now abandoned, which is a continuation of U.S. Ser. No. 07/785,804, filed Oct. 31, 1991, now abandoned; U.S. Ser. No. 08/195,487, filed Feb. 14, 1994, a continuation of U.S. Ser. No. 07/901,701, filed Jun. 22, 1992, now abandoned; U.S. Ser. No. 08/483,924, filed Jun. 7, 1995, which is a continuation of U.S. Ser. No. 08/195,487, filed Feb. 14, 1994, a continuation of U.S. Ser. No. 07/901,701, filed Jun. 22, 1992, now abandoned; U.S. Ser. No. 08/470, 950 filed Jun. 6, 1995, a divisional of U.S. Ser. No. 08/195, 487, filed Feb. 14, 1994, a continuation of U.S. Ser. No. 07/901,701, filed Jun. 22, 1992, now abandoned; U.S. Ser. No. 08/466,390 filed Jun. 6, 1995, a divisional of U.S. Ser. No. 08/195,487, filed Feb. 14, 1994, a continuation of U.S. Ser. No. 07/901,701, filed Jun. 22, 1992, now abandoned; and U.S. Ser. No. 08/467,781 filed Jun. 6, 1995, a divisional of U.S. Ser. No. 08/195,487, filed Feb. 14, 1994, a continuation of U.S. Ser. No. 07/901,701, filed Jun. 22, 1992, now abandoned.

BACKGROUND OF THE INVENTION

This invention relates generally to the use of body fluid-soluble nuclear matrix proteins as cellular markers. More particularly, the invention relates to a method of monitoring the degree of cell death in a tissue by monitoring the level of interior nuclear matrix proteins and/or fragments thereof released from cells in a body fluid-soluble form.

Cell death occurs as a function of healthy tissue homeostasis, as well as a result of disease or injury to the tissue. Detectable changes in the rate of cell death in a tissue therefore can provide an indication of the tissue's status. In normal growing tissue, for example, changes in the rate of cell death can indicate a new developmental stage. Alternatively, a sudden detected change in cell death in adult tissue can signal an injury to the tissue and also provide information on the type of injury. Previously, clinical assessment of tissue viability has required presentation of clinical symptoms and a visual inspection of the tissue itself, requiring observation of the morphology of cells in a tissue sample, and/or an indirect estimation of cell death by measuring changes in tissue/organ size. While the state of the art of morphological observation has advanced significantly, reliance on histological observation of an abnormality requires that the abnormal cells comprise part of the tissue sample tested. Early stages of a malignancy therefore can be particularly difficult to detect by this method. Biochemical assessments of cell or tissue viability also generally have been difficult to interpret, primarily because in many instances cell death occurs in individual cells which are intimately intermixed with viable cells in a sample.

There exists a need for reliable means of monitoring the degree of cell death in a tissue which does not rely on histology or tissue biopsy. A particularly useful method would be one wherein the rate of cell death could be monitored in a body fluid assay. It is anticipated that the ability to accurately monitor tissue-specific cell death in a fluid assay would have significant impact on the study of tissue development and cell kinetics, as well as on many different clinical applications. For example, the method may be used to monitor the progress of a disease or injury associated with cell death, as well as to monitor the efficacy of a therapy for an affected tissue. The method also may be used to monitor the effect of the therapy on unaffected, normal tissue. In addition, the method may be used to evaluate a compound's cytotoxicity.

Recently, methods have been disclosed for extracting and isolating the normally highly insoluble interior nuclear matrix proteins from cells. Interior nuclear matrix proteins are proteins from within the boundaries of the nuclear matrix, termed "interior" nuclear matrix proteins, which are substantially free of chromatin proteins, and intermediate filaments, collectively termed "exterior" nuclear matrix proteins (see Penman et al., U.S. Pat. No. 4,882,268, the disclosure of which is hereby incorporated by reference). In the method, the cell nucleus is isolated, the cytoskeleton proteins and chromatin are removed, the "nuclear matrix" is isolated, and the interior and exterior components of the nuclear matrix are separated. The nuclear matrix-intermediate filament complex comprises a specific fraction of cell protein constituting less than five percent of the total protein and six percent of the total DNA of the cell. The interior nuclear matrix comprises about one percent or less of the total cellular protein. It contains many proteins that differ according to cell type, and is highly enriched with type-specific antigens including cell-type and transformation-specific proteins that had not been detected using prior art procedures. It also contains the lamina and nuclear pore complex proteins. The separation method makes use of the unique properties of the nuclear matrix to achieve separation from substantially all other cell constituents. The method is simple, rapid, reproducible, achieves a high degree of purity, and is applicable to essentially all types of cells.

The method of Penman et al. has enabled the art to identify and isolate cell type-specific and transformation-specific interior nuclear matrix proteins of sufficient purity to allow antibodies to be made. These antibodies then can be used to detect cell type-specific interior nuclear matrix proteins in a sample, as disclosed in U.S. Pat. No. 5,273,877, issued Dec. 28, 1993, the disclosure of which is incorporated herein by reference. As used therein and here, the term "cell-type" is understood to refer to cells of various different tissues such as neural, glial, muscle, liver, mesenchymal, and different types of epithelia and endothelia, as well as malignant cell forms and cells having an altered genomic expression profile caused by viral infection or other factors.

It is an object of this invention to provide a method for monitoring the degree of cell death in a body fluid assay by monitoring the level of body fluid-soluble interior nuclear matrix proteins in a fluid. Another object of the invention is to provide a method for quantifying the body fluid-soluble interior nuclear matrix proteins released from cells and present in a cell compatible fluid. Still another object of the invention is to provide a method for evaluating a therapy, or the progress of a disease associated with cell death by monitoring the degree of cell death in an affected tissue. Another object of the invention is to provide a method for assessing the toxicity of compounds by assessing their ability to induce cell death. Still another object of the invention is to provide a method for inducing the release of body fluid-soluble nuclear matrix proteins from eucaryotic cells. These and other objects and features of the invention will be apparent from the description and claims which follow.

SUMMARY OF THE INVENTION

It now has been discovered that interior nuclear matrix proteins or soluble fragments thereof are released in soluble form from cells undergoing cell death. As used herein, "cell death" is understood to include both apoptosis ("programmed" cell death), and necrosis. Moreover, it also now has been discovered that these soluble forms of interior nuclear matrix proteins can be quantitated in a fluid and used to monitor the degree, or rate, of cell death in a tissue. The method of the invention also may be used to distinguish between types of cell death occurring. The presence of these proteins and protein fragments in solution in a body fluid soluble form is unexpected as the molecules comprise part of an insoluble nuclear complex under standard physiological conditions. The discovery of these proteins released in soluble form from dying cells allows one to use the soluble interior nuclear matrix proteins as biochemical monitors of tissue-specific cell death in fluid assays. The method is rapid and quantitative and can be used to evaluate the viability of cells and tissue, to evaluate progress of a disease and/or its treatment, to evaluate the cytotoxicity of unknown compounds and to study the kinetics of cell death. The discovery also provides an alternative method for purifying interior nuclear matrix proteins from cells.

The method of the invention involves detecting the concentration of body fluid-soluble interior nuclear matrix proteins or fragments thereof released from cells and comparing this concentration to a known standard. The concentration of these proteins in a body fluid sample will be indicative of the degree of cell death in that tissue. Fluid samples are collected at discrete intervals and detected by means, for example, of an immunoassay. The concentrations of characteristic proteins then are compared, with changes in concentrations being indicative of the changes in the rate of cell death. In addition, certain proteins may be identified as cell type-specific and/or as cell death type-specific. Exemplary body fluids include blood, serum, plasma, urine, semen, spinal fluid, saliva, ascitic fluid, peritoneal fluid, sputum, tissue swabs, and body exudates such as breast exudate.

In one embodiment of the invention, the method may be used to evaluate the progress of a disease. For example, the method may be used to monitor the progress of a malignancy such as, for example, a carcinoma, adenoma, sarcoma, lymphoma, or myeloma. Here the rate of cell death in a malignant tissue may be monitored by quantitating the level of soluble nuclear matrix protein released from the malignant cells. Alternatively, the method also may be used to monitor the progress of tissue disorders resulting in altered cell death, such as results from tissue atrophy, hyperplasia, cirrhosis, hypoxia, ischaemia and benign tumor growths. Injured tissue also can be assessed by this method, including direct cell trauma such as from membrane-active chemicals and toxins or resulting from direct physical trauma, such as, for example, hyperthermia, hypoxia and ischemia/ reperfusion, radiation or complement-mediated autolysis.

In another embodiment of the invention, the method may be used to monitor the efficacy of a therapy. Here a therapeutic agent or procedure (e.g., radiation therapy) is administered to a patient and, thereafter, the concentration of soluble nuclear matrix proteins or fragments are detected in body fluid samples drawn from the patient at predetermined intervals. These concentrations then are compared to each other and to those in samples tested before administration of the therapy. The changes in concentration of one or more interior nuclear matrix proteins detected among the samples compared will be indicative of the therapy's efficacy. For example, a therapeutic agent capable of selectively destroying malignant cells can cause an increase in soluble nuclear matrix proteins released from the tumor cells, followed by a reduction in the level of these proteins detected as the number of malignant cells fall. The method also may be used to monitor the effect of a given therapy on the viability of normal, unaffected tissue. For example, a number of cancer therapies, including radiation and chemotherapy, target rapidly proliferating cell populations and therefore can affect normally proliferative cell populations such as bone marrow progenitor cell populations and intestinal epithelial cells. The effect of the therapy on these cell populations can be evaluated by monitoring the level of soluble interior nuclear matrix protein released from these cells. It is anticipated that a single body fluid sample can provide information on the viability of both the affected tissue and normal tissue provided that cell-type specific proteins can be monitored for each tissue. Similarly, the method also may be used to evaluate the efficacy of complementary therapeutic agents designed to protect normal tissue from the effects of the therapy.

In yet another embodiment of the invention the method may be used to evaluate the type of cell death occurring and to study its kinetics. For example, nuclear matrix proteins or protein fragments may be identified that are preferentially released in soluble form by cells undergoing either apoptosis or necrosis. The rate of release of these proteins or protein fragments then may be monitored to investigate cell death kinetics.

In still another embodiment of the invention the method may be used to monitor the status of a cell culture and/or to assess the cytotoxicity of a compound by monitoring the levels of soluble interior nuclear matrix proteins or protein fragments released from these cells. Finally, the method also may be used to induce release of body fluid-soluble interior nuclear matrix proteins from intact cells, using compounds capable of inducing apoptosis, such as, for example, cytokines. A particularly useful cytokine is TNF (Tumor Necrosis Factor). This embodiment of the invention may be used to enhance identification of particular interior nuclear matrix proteins. It further may be used as part of a protocol to isolate soluble interior nuclear matrix proteins or protein fragments. Novel nuclear matrix proteins may be obtained by this method, as well as known or novel proteins useful as antigenic determinants in antibody production. Finally, the method of the invention may be useful as part of a protocol to identify candidate compounds useful as cancer chemotheapeutic agents (see infra.)

These and other embodiments and features of the invention will be apparent from the specification, drawings and claims, which follow.

BRIEF DESCRIPTION OF THE DRAWINGS

FIG. 1 (1.1 and 1.2) lists the levels of body fluid-soluble interior nuclear matrix protein quantitated in various normal and malignant tissue sample supernatants;

FIG. 2 lists the levels of body fluid-soluble interior nuclear matrix proteins quantitated in sera isolated from cancer patients and normal blood donors;

DETAILED DESCRIPTION

Figure 3:
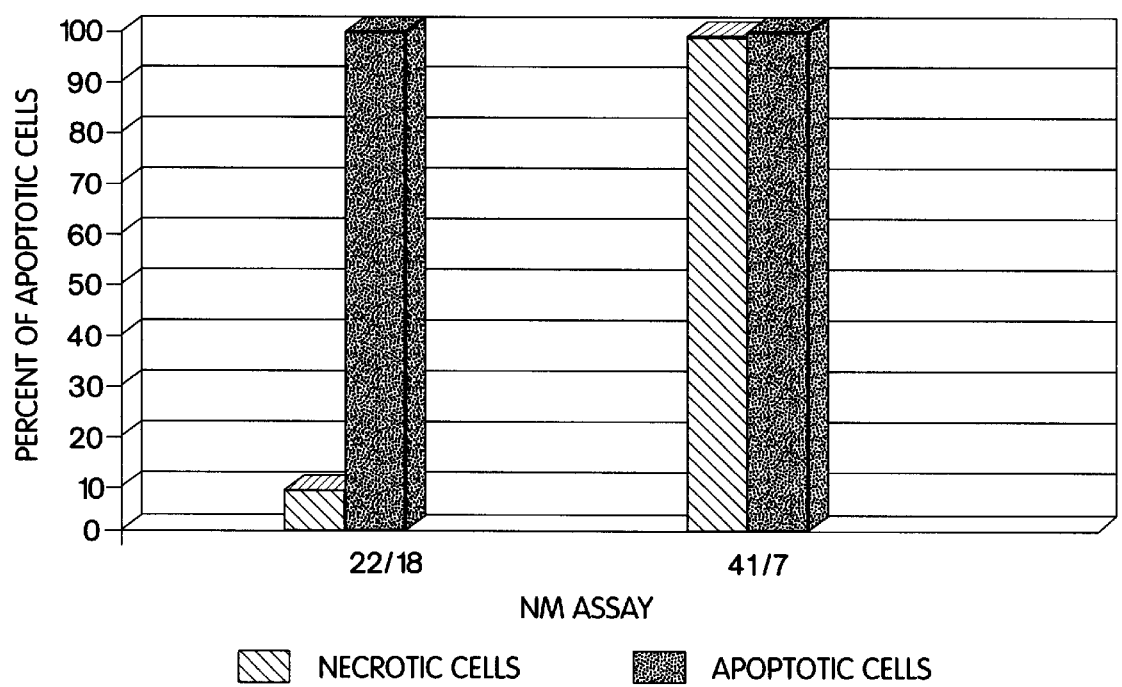
FIG. 3 is a graphic representation of the soluble nuclear matrix proteins detected by the 22/18 and 41/7 antibody combinations following the release of these nuclear matrix proteins from necrotic and apoptotic cells.

In the description which follows, the generalized method for monitoring cell death by quantitating the body fluid-soluble interior nuclear matrix proteins released from cells into a fluid is disclosed. The method involves the selection of interior nuclear matrix proteins to form a substantially pure preparation of interior nuclear matrix proteins, herein referred to as a NM preparation, and the use of this preparation to generate nuclear matrix protein-specific antibodies. Preferably the antibodies are cell-type specific. The antibodies also may be cell death-type specific. Next, methods are disclosed for designing assays useful for monitoring cell death with these antibodies in different fluid assays, including serum. Methods also are disclosed for inducing the release of these proteins in soluble form from cells.

Biologically relevant mechanisms of cell death generally are classified as either apoptosis or necrosis, primarily on the basis of histological studies. The two mechanisms generally are distinguished functionally and morphologically. Apoptosis generally is understood to characterize the coagulative necrosis of single cells, so-called "programmed" cell death. It characteristically affects individual cells in an asynchronous fashion, and generally is not accompanied by an inflammatory reaction. Apoptosis is involved in the programmed focal elimination of cells that accompanies embryonic and fetal development, and in regulating the size of organs and tissue in adult life. Apoptosis also has been identified in pathological tissue atrophy, as well as in a variety of malignant neoplasms, and following exposure to a range of injurious agents, a number of which are associated with DNA damage, e.g., radiation, hyperthermia, and a variety of carcinogens and cancer-chemotherapeutic agents. Cell-mediated immune reactions also are thought to induce apoptosis, and this mechanism of cell death also is associated with diseases highlighted by cell-mediated immune destruction of tissues, including so-called auto-immune diseases, cirrhosis, and a number of viral diseases including hepatitis and the like.

By contrast, necrosis generally is understood to refer to the progressive degeneration of cell structure that occurs after death caused by severe, injurious changes in environmental conditions. Necrosis typically affects groups of contiguous cells and an inflammatory reaction usually develops in the adjacent viable tissue. Among the many known examples of necrosis are cell destruction following severe hypoxia and ischemia, in tissue undergoing autolysis in vitro, and cell destruction following severe hyperthermia, or exposure to numerous membrane-active chemicals, toxins and reactive oxygen metabolites.

Morphologically, necrotic cells tend to appear swollen, with eosinophilic cytoplasm and indistinct cell boundaries. Cells undergoing apoptosis are characterized by chromatin condensation and by the formation of membrane-bound apoptotic bodies.

All eukaryotic cells, both plant and animal, have a nucleus surrounded by the cell cytoplasm. The nucleus contains DNA complexed with protein and termed chromatin. The chromatin, with its associated proteins, constitutes the major portion of the nuclear mass. The chromatin is organized by the internal protein skeleton of the nucleus referred to herein as the interior nuclear matrix. A method for extracting and selectively purifying the highly insoluble interior nuclear matrix protein from cells recently has been discovered (see U.S. Pat. No. 4,882,268 incorporated herein by reference). It also has been discovered that certain interior nuclear matrix proteins are tissue and cell type-specific and that their expression also can be altered in a transformation- or disease-specific manner in affected cells. This alteration in expression pattern makes these proteins ideal markers for detecting and identifying abnormal cell growth, particularly for detecting malignancies, (see U.S. Pat. No. 5,273,877 issued Dec. 28, 1993, incorporated herein by reference). Following the methods disclosed in the U.S. Pat. Nos. 4,882,268 and 4,885,236 patents, interior nuclear matrix proteins can be selectively purified and used as antigenic determinants to raise antibodies which may be used to detect the presence of these proteins in cell samples or as part of the cellular debris from destroyed cells.

A detailed description for isolating interior nuclear matrix proteins is disclosed in U.S. Ser. No. 214,022 filed Sep. 30, 1988 and incorporated by reference herein (see supra). Broadly, the isolation procedure involves the following:

1. Isolation and separation of cells.
2. Separation of soluble cell proteins from the nucleus and cytoskeleton by extraction of membrane lipids and soluble proteins with a non-ionic detergent-physiological salt solution.
3. Separation of cytoskeleton proteins from the nucleus by solubilization of the insoluble cell material from step 2 in either 0.25M ammonium sulfate, pH 6.8, a detergent-sodium deoxycholate solution, or other gentle extraction buffer.
4. Separation of chromatin from the nuclear matrix by digestion of the insoluble material from step 3 with DNAse I and RNAse in a physiological buffer, and elution of the DNA-containing nucleosomes with 0.25M ammonium sulfate solution buffered to pH 6.8 or other gentle extraction buffer.
5. Separation of the interior nuclear and "exterior" nuclear matrix proteins by dissolution of the insoluble material from step 4 in a buffer containing between 5 and 10M urea, preferably 8M urea, or other suitable solubilizing agent, and aggregation of the exterior proteins by dialysis into physiological buffer.

In a variation of this procedure, and as used herein, the cytoskeleton proteins and chromatin are removed together by digesting the insoluble material from step 2 with DNAse and RNAse, then extracting with 0.25M ammonium sulfate at ph 6.8. Further purification of the interior nuclear proteins can be performed using standard methods known to those skilled in the art, including HPLC, FPLC, chromatofocusing and the like.

The matrix preparation is biochemically and morphologically pure by several biochemical criteria. Freedom from contamination permits a clear and detailed analysis of the matrix proteins by gel electrophoresis. It previously has been shown that electropherograms of a NM preparation show markedly different patterns in different cell types.

These patterns are unique, specific and reproducible. It further has been discovered that this pattern allows selection of one or more proteins characteristic of the cell type and useful as antigenic determinants. (See, for example, U.S. Pat. No. 4,882,268 and U.S. Pat No. 5,273,877) As shown therein, individual matrix proteins useful as cell-type discriminators often comprise less than 0.01% of the cell's total protein. Antibodies raised against these proteins then can be used to identify cell-type specific nuclear matrix proteins in samples. Moreover, antibodies raised against these proteins also may be used to distinguish the type of cell death occurring (see infra.)

As indicated above, the method of the invention involves monitoring cell death by quantitating the soluble interior nuclear matrix proteins released from cells into a fluid. As will be appreciated by those skilled in the art, any means for specifically identifying and quantifying the protein is contemplated. The current state of the art for identifying proteins in solution is by means of an immunoassay, wherein an antibody capable of binding specifically to the protein of interest is used to identify the protein in solution and the amount of bound complex formed then is determined.

Antibody methodologies are well understood and described in the literature. A more detailed description of their preparation can be found, for example, in *Practical Immunology,* Butt, W. R., ed., Marcel Dekker, New York, 1984. Broadly, antibodies may be raised against one or more proteins in a NM preparation by immunizing a suitable animal with an immunogenic preparation under conditions sufficient to induce antibody production in that animal. Monoclonal antibodies then can be obtained by fusing suitable antibody producing cells such as spleen or lymph node cells to myeloma cells and screening the fusion products for nuclear reactivity against the immunogen source (e.g., cell line or particular cell type determinant) using standard techniques. A detailed protocol for screening for particular cell type determinants can be found in U.S. Ser. No. 214,022, incorporated by reference hereinabove.

The currently preferred method for quantitating body fluid-soluble nuclear matrix proteins is by detecting the proteins with interior nuclear matrix protein-specific antibodies. The antibodies may be monoclonal or polyclonal in origin, and may be produced by standard methodologies. The nuclear matrix proteins used as immunogens may be prepared by the method disclosed by Penman et al. (U.S. Pat. No. 4,882,268, see infra). Alternatively, interior nuclear matrix proteins may be isolated by inducing their release in soluble form from cells as described herein, and selectively extricating them from the supernatant. Proteins or protein fragments also may be recombinantly expressed from nucleic acids using standard recombinant DNA technology. Antibodies to one or more of these proteins then are raised using standard methods. The antibodies then are exposed to the body fluid sample under conditions sufficient to allow specific binding of the antibody to its specific nuclear matrix protein, and the amount of complex formed then detected.

A variety of different forms of immunoassays currently exist, all of which may be adapted to quantitate body fluid-soluble interior nuclear matrix proteins released from cells. Of the various immunoassay formats available, one of the most sensitive is the sandwich technique. In this method, two antibodies capable of binding the analyte of interest are used: one immobilized onto a solid support, and one free in solution, but labeled with some easily detectable chemical compound. Examples of chemical labels that may be used for the second antibody include radioisotopes, fluorescent compounds, and enzymes or other molecules which generate colored or electrochemically active products when exposed to a reactant or enzyme substrate. When samples containing analyte (e.g., body fluid-soluble interior nuclear matrix protein or protein fragments) are placed in this system, the analyte binds to both the immobilized antibody and the labelled antibody. The result is a "sandwich" immune complex on the support's surface. The analyte is detected by washing away nonbound sample components and excess labeled antibody and measuring the amount of labeled antibody complexed to analyte on the support's surface. The sandwich immunoassay is highly specific and very sensitive, provided that labels with good limits of detection are used. A detailed review of immunological assay design, theory and protocols can be found in numerous texts in the art, including *Practical Immunology,* Butt, W. R., ed., Marcel Dekker, New York, 1984.

Immunoassay design considerations include preparation of antibodies (monoclonal or polyclonal) having sufficiently high binding specificity for their antigen that the specifically-bound antibody-antigen complex can be distinguished reliably from nonspecific interactions. The higher the antibody binding specificity, the lower the antigen concentration that can be detected. The choice of tagging label for the second antibody also will depend on the detection limitations desired. Enzyme assays (ELISAs) typically allow detection of a colored product formed by interaction of the enzyme-tagged complex with an enzyme substrate. Alternative labels include radioactive or fluorescent labels. The most sensitive label known to date is a chemiluminescent tag where interaction with a reactant results in the production of light. Useful labels include chemiluminescent molecules such as acridium esters or chemiluminescent enzymes where the reactant is an enzyme substrate. When, for example, acridium esters are reacted with an alkaline peroxide solution, an intense flash of light is emitted, allowing the limit of detection to be increased 100 to 10,000 times over those provided by other labels. In addition, the reaction is rapid. A detailed review of chemiluminescence and immunoassays can be found in Weeks, et al., (1983) *Methods in Enzymology* 133:366–387. Other considerations include the use of microtiter wells or column immunoassays. Column assays may be particularly advantageous where rapidly reacting labels, such as chemiluminescent labels, are used. The tagged complex can be eluted to a post-column detector which also contains the reactant or enzyme substrate, allowing the subsequent product formed to be detected immediately.

The invention may be better understood from the following nonlimiting examples wherein interior nuclear matrix proteins are prepared from two different cell lines (breast tumor and cervical tumor cells), polyclonal and monoclonal antibodies are made and tested for reactivity and sensitivity, and immunoassays are performed on sera, and tissue and cell culture supernatants. Apoptosis generally is induced herein by placing cells in serum-free media, by exposure to a cytokine (e.g., TNF) or by exposing cells to particular cytotoxic agents. Necrosis is induced herein by freeze thawing (hyperthermia.) Using the methods disclosed herein, and variations of these methods, cell death can be quantitated and monitored in vivo and in vitro by analyzing body fluids or body fluid compatible solutions, e.g., extracellular culture media, for soluble nuclear matrix proteins or protein fragments. Generally, the method involves preparation of a standard ("dose response") curve for the nuclear matrix protein to be monitored, and against which samples can be prepared. As indicated earlier, the status of multiple different tissues also may be assessed in a single fluid sample, by monitoring the concentrations of different cell-type specific nuclear matrix determinants in the sample.

Also disclosed is a method for inducing release of interior nuclear matrix proteins in soluble form from cells, using compounds capable of inducing cell death. Currently preferred compounds include cytokines such as TNF which induce apoptosis. Inducing release of interior nuclear matrix proteins from cells into a fluid can enhance evaluation of a tissue's status. It also is envisioned that the method may be useful as part of a protocol for identifying and purifying novel interior nuclear matrix proteins, for preparing proteins and protein fragments for use as antigens in antibody preparations, and for identifying candidate compounds useful in cancer chemotherapy (see infra.)

I. Antibody Development

A. Isolation of Nuclear Matrix

Nuclear matrix proteins are isolated herein essentially according to the method of Penman and Fey, disclosed in U.S. Pat. No. 4,882,268, the disclosure of which is incorporated herein by reference. Briefly, desired cell lines are grown to confluency in Dulbecco's Modified Eagle's medium (DME) (Mediatech, Washington, D.C.) with 10% fetal calf serum (Hazelton) in T225 flasks. The media then is removed from the flask and the cells washed twice with phosphate buffered saline (PBS) (0.1M Phosphate, 0.15M NaCl pH 7.4). The washed cells then are removed from the flask by incubation with 0.1% tryspin/EDTA (Irvine Scientific, Santa Ana, Calif.) in PBS at 37° C. for 15 minutes. The resulting cell suspension is poured into 10 ml of the original media and pelleted by centrifugation at 1500×g for 15 min. The media then is aspirated off and the cells resuspended, and counted. The cells are again pelleted and extracted twice with cold RSB/Majik buffer (0.1M NaCl, 10 mM $MgCl_2$, 10 mM TRIS, 0.5% Na Deoxycholate, 1.0% Tween-20, 1.2 mM PMSF pH 7.4) and spun at 2100×g for 15 min at 4° C. 10 ml of RSB/Majik is used for every 1×10E7 cells. At room temperature the extracted cells are resuspended in digestion buffer (50 mM NaCL, 300 mM sucrose, 0.5% Triton X-100, 10 mM PIPES, 3 mM $MgCl_2$, 1 mM EGTA, 1.2 mM PMSF). DNase I and RNase A (Boehringer Mannheim, Germany) are added to a concentration of 100 ug/ml and the solution incubated with agitation for 20–40 min. Sufficient 2M ammonium sulphate is added to make a final concentration of 0.25M and after 5 min the solution is centrifuged at 3700×g for 15 min. The resulting pellet is resuspended in disassembly buffer (8M urea, 20 mM MES, 1 mM EGTA, 1.2 mM PMSF, 0.1 mM $MgCl_2$, 1% 2-mercaptoethanol pH 6.6) and dialyzed against 4 liters of assembly buffer (0.15M KCl, 25 mM Imidazone, 5 mM $MgCl_2$, 2 mM dithiothreitol, 0.125 mM EGTA, 0.2 mM PMSF pH 7.1) overnight at room temperature. The resulting suspension is then centrifuged in an ultracentrifuge at 100,00 g for one hour. The supernatant containing the interior nuclear matrix proteins (referred to herein as the NM preparation) then can be stored frozen at −80° C. until required.

For the examples disclosed herein, interior nuclear matrix proteins were isolated from three human tumor cell lines, all available through the American Type Culture Collection (ATCC, Rockville, Md.): T-47D (a breast tumor cell line); and ME-180 and CaSki (both cervical tumor cell lines).

B. Immunization Protocols

1. Polyclonal Antibodies

Polyclonal antisera can be raised against the NM preparation using standard methodologies, such as those disclosed in numerous texts available in the art and known to those generally skilled in the art. In this example, rabbits were immunized with the NM preparations first in Freund's complete adjuvant (Gibco, Grand Island, N.Y.) and then every month with NM with incomplete adjuvant for three months. Rabbit sera and sera from mice prior to fusion were used as polyclonal antisera and were shown by standard western blot technique to be reactive with the NM preparations.

2. Monoclonal Antibodies

Monoclonal antibodies can be raised against the NM proteins also using standard methodologies, such as those disclosed in numerous texts available in the art and known to those generally skilled in the art. In this example, Balb/c by J (The Jackson Laboratory, Bar Harbor, Me.) mice were immunized with the nuclear matrix protein preparations in the following manner:

(a) Lymph Node Protocol: Animals are injected in the two hind foot pads and hind quarters using the following protocol: day 1, Antigen and complete Freund's Adjuvant; day 4, antigen and saline in hindquarters only; day 13, the animal is sacrificed and the popliteal lymph nodes removed for fusion.

(b) Spleen Protocol: Animals are injected every two weeks intraperitoneally for 6–8 injections, then boosted intravenously once four days prior to sacrifice and removal of the spleen. Injection #1 is with complete Freund's adjuvant, #2 is incomplete adjuvant, and subsequent injections are with saline.

C. Fusions

Hybridomas of the spleen or lymph node cells are fused essentially accordingly to the method of Kohler and Milstein (1975) *Nature* 256:495, the disclosure of which is herein incorporated by reference. Briefly, a suspension of spleen or lymph node cells are fused with cells of a mouse myeloma cell line using polyethylene glycol (PEG, Boehringer Mannheim). Resulting positive hybridomas then are cloned a minimum of three times to achieve monoclonicity. Mouse myeloma cell lines used herein were SP2/0-Ag14 or P3X63Ag8.653 (ATCC, Rockville, Md.)

1. Antibody Screening (Cell Assay/Reactivity Assay)

Growth positive wells from the hybridomas can be screened for nuclear reactivity against the cell line that is the source of the immunogen using the minifold I dot blot apparatus (Schleicher & Schuell, Keene, N.H.) and standard procedures. Briefly, a 4.5" by 3" piece of nitrocellulose 0.45 μm filter membrane (Bio-Rad, Richmond, Calif.) and two pieces of similar size Whatman 3 MM paper are soaked in distilled water and PBS for 10 min each and then assembled in the dot blot apparatus. 1×10E6 cells stored frozen in 10% DMSO culture media are washed in PBS and 100 μl per well of a 10 ml cell suspension are added with the vacuum suction on. The cells then are washed with 100 μl of digestion buffer, 400 μl of PBS with 0.05% Tween-20, 100 μl of 0.5% nonfat dried milk (Carnation) in PBS (to block nonspecific binding), and 400 μl of PBS Tween-20. With the vacuum turned off, 100 μl of supernatant from growing hybrids are incubated with the cells for 30 min. The supernatant then is removed via vacuum suction and the cells again washed with 400 μl of PBS Tween-20. With the vacuum off, 100 μl of a goat anti-mouse biotin conjugate in 1% horse serum PBS (e.g., VECTASTAIN, Vector labs, Burlingame, Calif.) is added to each well and incubated for 15 min. The cells then are washed with 400 μl of PBS Tween-20 and incubated with the Vectastain Avidin-HRP substrate for 3 min. The reaction is stopped with tap water and the membrane removed from the apparatus and soaked in water. The membrane then is sandwiched between two glass plates with microscope slide resin and examined under the microscope. Wells showing positive nuclear staining are considered positive and these hybrids are chosen to be further cloned.

2. Tissue Immunohistochemistry

Positive clones can be evaluated for human tissue reactivity using cryostat cut frozen tissue sections and the avidin/biotin peroxide staining procedure. (Vectastain Elite ABC kit, Vector Laboratories, Burlingame, Calif.)

3. Ascites Production

Mice are pristane (2,6,10,14 Tetramethylpentadecane) primed by injecting 0.5 ml pristane into the peritoneal cavity. Seven to ten days later 5×10E6 cells in one ml of serum free media are injected into the peritoneal cavity. Ascites fluid then is collected from each mouse twice and pooled. Monoclonal anti-NM antibodies are purified from mouse ascites by protein G purification (Genex Corp., Gaithersburg, Md.) and stored at 4° C. until required.

D. Biotinylation of Antibodies

Antibodies can be labelled following standard techniques. In these examples, antibodies are biotinylated conventional procedures. Briefly, purified antibodies (herein, monoclonal anti-NM antibodies purified from mouse ascites) are dialyzed overnight against 0.1M sodium bicarbonate pH 8.4 and the concentration adjusted to 1.0 mg/ml. Biotin-X-NHS (0.5 ml CalBiochem, Inc., San Diego, Calif.) 1.5 mg/ml in DMSO, then is added to 5 ml of the antibody solution and reacted for 2 hr at room temperature with rocking in the dark. 2M Tris-HCL pH 8.0 (0.5 ml) is added and incubated for a further 30 min. PBS-merthiolate (0.01%) containing 1% BSA then is added (5 ml) and the mixture dialyzed three times against the PBS-Merthiolate.

II. Assays

A. Sandwich Immunoassay (ELISA)

A standard immunoassay can be performed to generate dose response curves for antigen binding, for cross reactivity assays, and for monitoring assays. The data is generated with a standard preparation of NM antigen, and is used as the reference standard when body fluids are assayed. In these examples both ELISAs and radioummunoassays were performed.

1. Immunoassay (Well Assay)

Microtitre plates (Immulon II, Dynatech, Chantilly, Va.) are coated with purified antibody at 5 to 15 ug/ml in PBS at pH 7.4 for 1 hr or overnight and then washed 3× with 300 μl PBS. The plates then are blocked with 10% normal goat serum in PBS for 1 hr at room temp and washed 3× with 300 μl of PBS.

Here, samples were assayed by pipetting 100 μl of sample per well, and incubating for 1 hr at RT. The wells were washed with 3×300 μl PBS. 100 μl of 1.25 to 10 μg/ml of a biotinylated antibody was added to each well, incubated for 1 hr at RT and washed with 3×300 μl of PBS. 100 μl of a 1:1000 dilution of streptavidin-horseradish peroxidase conjugate (The Binding Site Ltd., Birmingham, UK) was added to each well and incubated for 1 hr and then washed with PBS. 100 μl of peroxidase substrate (citrate, phosphate, OPD-$H_2O_2$) was added to each well and incubated for 20 min. The reaction was stopped by adding 50 μl of 1M $H_2SO_4$ to the wells. The optical density was read on a plate reader at 490 nm.

Concentrations of NM antigen were determined by preparing a reference concentration of NM and preparing a standard dilution curve to compare with the unknown samples.

2. IRMA (Immunoradiometric Assay)

(a) Iodination of Streptavidin

10 μg of streptavidin (Sigma, Inc., Cincinnati) in 2 μl of 0.05M phosphate pH 7.4 was added to 10 μl of 0.25M phosphate pH 7.4 in a microcentrifuge tube and 1 mCi of $^{125}$I (NEN-DUPONT, Wilmington, Del.) in 10 μl was added. Immediately 10 μl of 100 mg chloramine-T trihydrate (Sigma, Inc.) in 50 ml of distilled water was added, mixed, and reacted for 25 sec. The reaction was stopped by mixing for 20 sec with 50 μl of 40 mg Cysteamine (2-mercaptoethlyamine) (Sigma, Inc.) and 5 mg KI in 50 ml of 0.05M phosphate pH 7.4. 0.5 ml of 1% BSA in PBS pH 7.4 was added and the material was fractionated on a 10 ml sephadex G-100 column (Pharmacia, Sweden) pre-equilibrated with the BSA PBS buffer. 30 by 0.5 ml fractions were collected and 10 μl was diluted to 1 ml of the BSA/PBS buffer for each fraction. 100 μl of the diluted fraction was counted on a LKB gamma counter set for $^{125}$I. The specific activity was calculated and routinely fell between 85 to 100 uCi/ug. The mid fractions of the protein peak were used in the sandwich immunoassay.

(b) Sandwich Radioimmunoassay

The microtitre breakaway wells (Immulon II Removawell strips, Dynatech, Chantilly, Va.) are coated and blocked as in the ELISA assay. The samples, standard or sera, are routinely measured by incubating 100 μl in the wells for 1 hr at RT washing on a plate washer with 3×300 μl of PBS and then incubated with the biotinylated antibody (2–10 μg/ml in 10% goat serum) for 1 hr at RT and washed again. The bound biotinylated antibody is detected with the $^{125}$I-streptavidin. 200,000 to 300,000 cpm (77% counter efficiency) in 100 μl is added to each well and incubated for 1 hr at RT and washed again. The bound fraction is detected by counting the radioactivity in an LKB gamma counter. The concentration can be determined by comparing the counts obtained against a reference preparation.

B. Dot Blot Detection of NM

Antibody reactivity with NM proteins can be assessed by dot blot detection assays, using standard methodologies and apparatus (e.g., Schleicher & Schuell). Nitrocellulose membranes are soaked in Tris buffered saline, (TBS, 50 mM TRIS, 150 mM NaCl, pH 7.6) and NM preparation applied at varying concentrations of protein to a series of wells and incubated for 1 hr at room temperature (e.g., T-47D NM supernatant at 10 μg/ml, 1 μg/ml and 100 ng/ml). The blocked wells then are washed with 2×200 μl of TBS and then blocked with 100 μl 10% normal goat serum in TBS for 1 hr at room temperature. The blocked wells then are washed again with 2×200 μl of TBS and 100 μl of culture supernatant containing nuclear reactive antibody to be tested is added to their respective wells and incubated for 1 hr at room temperature. The wells then are washed with 2×200 μl of TBS and 100 μl of a dilution series of alkaline phosphatase conjugated goat anti-mouse IgG (Bio-Rad, Richmond, Calif.) (e.g., 1:1000, 1:5000, or 1:10000) added to the relevant wells and incubated for 1 hr. The wells then are washed with 2×200 μl of TBS followed by addition of enzyme substrate (BCIP/NBT, Kirkgaard and Perry, Gaithersburg, Md., e.g., 100 μl) in Tris buffer containing Levamisole (Vector, Inc., Corpus Christi, Tex.) A fifteen minute incubation generally is sufficient. The reaction can be stopped by washing with distilled water and the product detected.

III. Soluble Antigen Preparation from Dying Cells (Serum Deprivation)

Cell lines are grown to confluency in tissue culture flasks by standard culturing techniques. The media then is replaced with serum-free media and the cells placed in a 37° C. incubator with 5% $CO_2$ for 7 to 14 days, depending on the cell line. At the end of the incubation the media is collected and centrifuged at 14,000×g to remove cellular debris, and the supernatant stored frozen.

Where human tissue is used, normal and tumor, the soluble interior nuclear matrix proteins can be released in a similar fashion. Tissue is removed from a donor, flash frozen in liquid nitrogen within 10 min to 4 hrs after removal and stored at −70° C. until required. When ready to be used, the tissue is chopped into 0.1 to 0.3 cm cubes as it thaws using aseptic techniques in a laminar flow hood and placed in a T150 flask containing serum free media containing Fungizone and gentamycin. In general, 2–4 g of tissue are used per 100 ml media in the T150 flask. The flask containing the tissue then is incubated for 4–7 days at 37° C. with 5% $CO_2$. After incubation the media is collected from the flasks, centrifuged at 14,000×g for 20 min and the supernatant stored at −20° C. until needed.

IV. Representative Assays
Reactivity Assays

Immunoblot studies for anti-nuclear matrix reactivity were performed with monoclonal antibodies raised against T-47D nuclear matrix to identify those having strong reactivity with the T-47D antigen. Among those identified were three antibodies referred to herein as 200-4, 203-37, and 304-41. All antibodies exhibited a positive reaction. The intensity of reaction was best at the higher concentrations of secondary antibody, and no reaction was observed in the absence of antigen.

Using the same assay conditions these three antibodies, 200-4, 203-37, and 304-41, all showed reactivity with the supernatant from T-47D dying cells, but not with the media alone, demonstrating the release of soluble antigen into the cell culture supernatant. Anti-KLH (keyhole limpet hemocyanin) monoclonal antibody used as a negative control, showed no reactivity with the spent supernatant confirming the specificity of the antibody reactions. Similar results were obtained with polyclonal rabbit sera raised against the nuclear matrix proteins.

Table I below displays the binding results for assays performed with different antibodies raised against the two different cervical tumor cell line NM antigen preparations (ME-180 and CaSKi). The 100-series antibodies are those raised against the ME-180 NM immunogen; the 300-series are those raised against CaSKi-NM immunogen.

TABLE I

| CAPTURE Ab | SOLUTION Ab | | | | | |
|---|---|---|---|---|---|---|
|  | 107-7 | 302-18 | 302-22 | 302-29 | 302-47 | 307-33 |
| 107-7 | NO RXN | NO RXN | NO RXN | RX | NO RXN | RXN |
| 302-18 | NO RXN | RXN | RXN | RXN | RXN | RXN |
| 302-22 | NO RXN | RXN | NO RXN | NO RXN | NO RXN | RXN |
| 302-29 | NO RXN | RXN | NO RXN | NO RXN | NO RXN | RXN |
| 302-47 | NO RXN | NO RXN | NO RXN | NO RXN | NO RXN | NO RXN |
| 307-33 | NO RXN | NO RXN | NO RXN | RXN | NO RXN | RXN |

As can be seen from the table, twelve of the thirty-six combinations tested result in a positive reaction. A positive reaction means that the two antibodies react with different epitopes on the same molecule. Only one antibody, 302-18, reacted in combination with itself.

Dose Response Assays

The first sandwich assay was obtained using antibodies 200.34 and 200-4 on nuclear matrix proteins isolated by the method of Penman and Fey (Table II) and on cell culture supernatant from dying cells (Table III). The cell line T-47D was used as the source of antigen for both experiments and demonstrated that a dose response curve can be obtained with these assay conditions.

Table II shows the data generated using a standard ELISA immunoassay and purified NM, isolated by the method of Penman et al. Table III shows the data generated under the same conditions, but using the supernatant of dying cells as the antigen source. The cell line T-47D was used as the antigen source for both experiments and two antibodies, previously shown to have strong reactivity with the T-47D antigen by dot blot assay, were used (Ab 200-34, solid phase; Ab 200-4 as soluble antibody).

TABLE II

| Protein Concn. | OD | | |
|---|---|---|---|
| in NM prep. | rep 1 | rep 2 | mean |
| 10 µg/ml | 0.186 | 0.187 |  |
| 1 µg/ml | 0.036 | 0.032 | 0.034 |
| 0.1 µg/ml | 0.021 | 0.009 | 0.015 |
| 0.0 | 0.00 | 0.003 | 0.001 |

TABLE III

| Concentration of supernatant | Mean OD | SD |
|---|---|---|
| Undiluted | 0.150 | 0.015 |
| 1:2 | 0.071 | 0.010 |
| 1:4 | 0.026 | 0.003 |
| 1:8 | 0.013 | 0.005 |
| No Sup |  |  |
| 2:1 | 0.401 | 0.015 |
| undiluted | 0.145 | 0.006 |
| 1:2 | 0.05 | 0.002 |
| 1:4 | 0.017 | 0.003 |
| 1:8 | 0.003 | 0.002 |
| No Sup | 0.000 |  |

The data show that reliable dose response curves can be generated using these assay conditions to quantitate soluble NM antigen in solution. Following this protocol, other antibody combinations can be tested for their ability to detect and quantitate body fluid-soluble nuclear matrix proteins and protein fragments.

Dose response evaluation results of two of these antibody combinations are shown in Table IV, below, using ME-180 cell culture supernatant as the antigen source. Each assay shows dose dependent detection of antigen in the tissue culture supernatant, demonstrating the ability of the assay to quantitate soluble interior nuclear matrix protein released from dying cells.

TABLE IV

| Concentration of supernatant | Mean OD | SD |
|---|---|---|
| Antibody 107-7 solid phase, 302-29 soluble antibody, ME-180 supernatant | | |
| 2:1 | 0.501 | 0.013 |
| undiluted | 0.274 | 0.018 |
| 1:2 | 0.127 | 0.006 |
| 1:4 | 0.067 | 0.006 |
| 1:8 | 0.035 | 0.009 |
| 1:16 | 0.021 | 0.007 |
| No Sup | 0.000 |  |

TABLE IV-continued

| Concentration of supernatant | Mean OD | SD |
|---|---|---|
| Antibody 107-7 solid phase, 307-33 soluble antibody, ME-180 supernatant | | |
| 3:1 | 0.906 | 0.009 |
| 3:2 | 0.456 | 0.011 |
| 3:4 | 0.216 | 0.007 |
| 3:8 | 0.099 | 0.005 |
| 3:16 | 0.052 | 0.002 |
| 3:32 | 0.031 | 0.005 |
| No Sup | | |

Next, interior nuclear matrix protein quantification was tested in supernatant from a variety of dying tumor tissues. Here, tumor and normal tissues were allowed to die in media as described supra. Supernatants were assayed in various configurations of sandwich assays. The results are shown in FIG. 1, where all values are in units/gm, using ME-180 antigen as standard. As can be seen from FIG. 1, antigen is released from each of the dying tissues, and the three assays are measuring different antigens. As expected, the increased cell death in tumor tissue is reflected in a higher average antigen value quantitated in cancer tissue versus normal tissue. In addition, significant differences in antigen quantities are seen in the different tissue sources, indicating that the soluble antigen quantities present in the supernatant vary in a cell-type specific manner.

FIG. 2 shows the results of an analogous experiment performed using serum samples from cancer patients and normal blood donors. As for FIG. 1, ME-180 cell antigen was the standard. Results are reported in units/ml. A control experiment diluting supernatant antigen into serum and then quantitating the protein in solution indicates that serum has little or no effect on the assay. As can be seen in FIG. 2, like the results shown in FIG. 1, serum samples from cancer patients reflect a higher rate of cell death as indicated by the quantifiably higher levels of antigen detected in these samples compared with those detected in the normal blood serum samples.

Apoptosis and Necrosis

1. In this example, both apoptosis and necrosis were induced and the effect of this injury on nuclear matrix protein release tested. In this experiment ME-180 cells (cervical tissue culture cell line) were suspended into serum free medium. Necrosis was induced in one aliquot by freezing the cells at $-20°$ C., overnight. Cells were allowed to necrose for seven days at $37°$ C. with 5% $CO_2$. Apoptosis was induced in a second aliquot by serum deprivation for seven days at $37°$ C. with 5% $CO_2$. Supernatants from each aliquot then were harvested and assessed by immunoradiometric assays using 302-22/302-18 ("22/18") and 204-41/107-7 ("41/7") antibody combinations. As shown in FIG. 3, the 22/18 assay shows specificity for apoptosis: ten times more 22/18 antigen is released by apoptotic cells (serum deprived, non-frozen) than by necrotic cells (frozen). By contrast, the 41/7 assay measures an antigen that is released substantially equally by both necrotic and apoptotic cells.

2. In this example apoptosis was induced by exposing MCF 7 cells (breast carcinoma cell line, ATCC, Rockville, Md.) to Tumor Necrosis Factor (TNF alpha). MCF 7 cells were seeded into 12 individual T-25 flasks in 35 ml of Dulbecco Modified Media (DME) with 5% fetal calf serum and SeraXtend. The cells were grown at $37°$ C. and 5% $CO_2$ until 60–70% confluency. Cell supernatants were removed and split into two groups of six:

Group 1: Control—cell supernatants were replaced with fresh media.

Group 2: TNF—Cell supernatants were replaced with fresh media containing 500 U/ml recombinant human TNF-alpha (Cellular Products, Inc. (Buffalo, N.Y.).

Figure 4A:
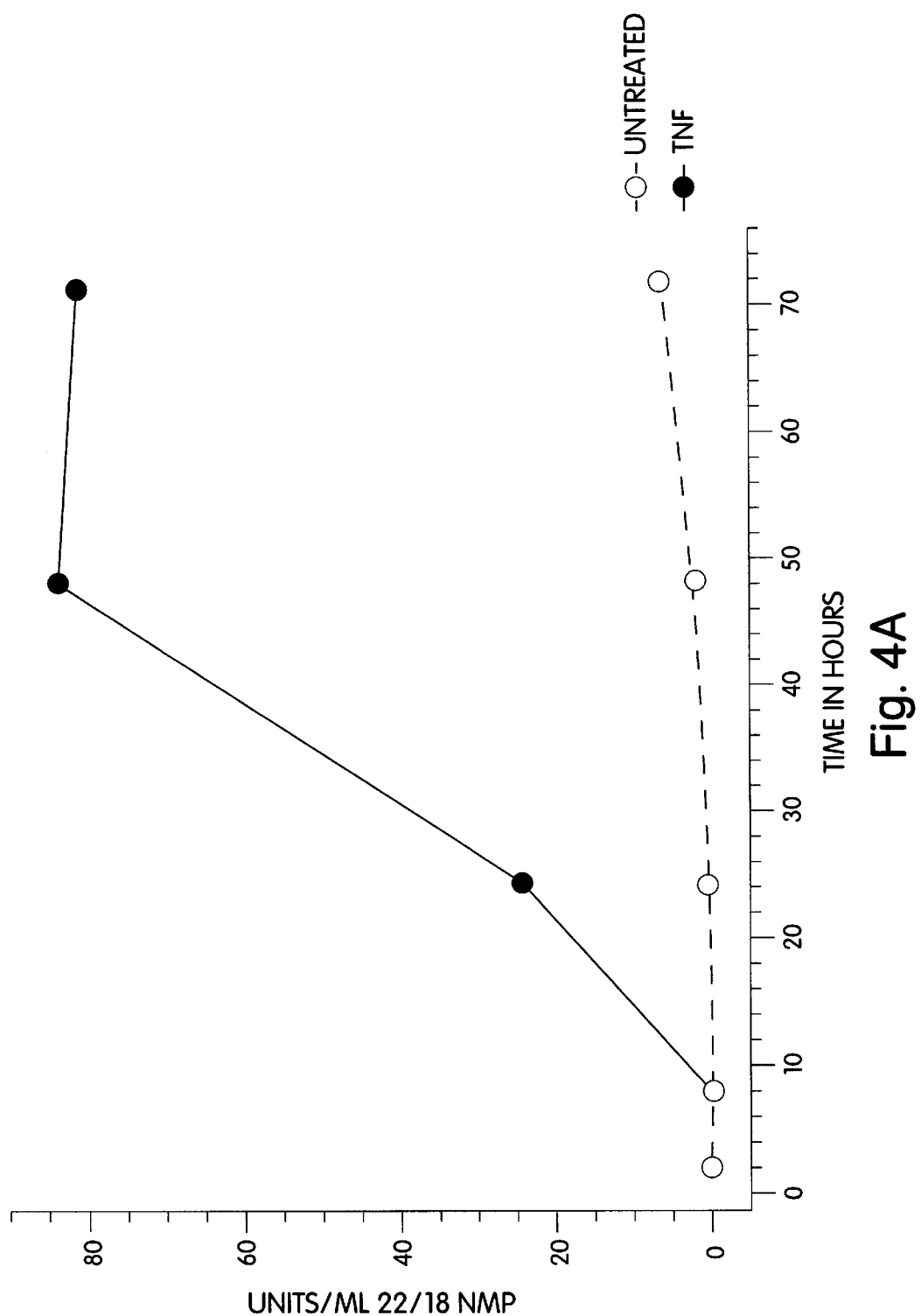
FIG. 4 (A and B) are graphic representations of the effect of TNF (tumor necrosis factor) on soluble nuclear matrix protein released from cultured cells.
Figure 4B:
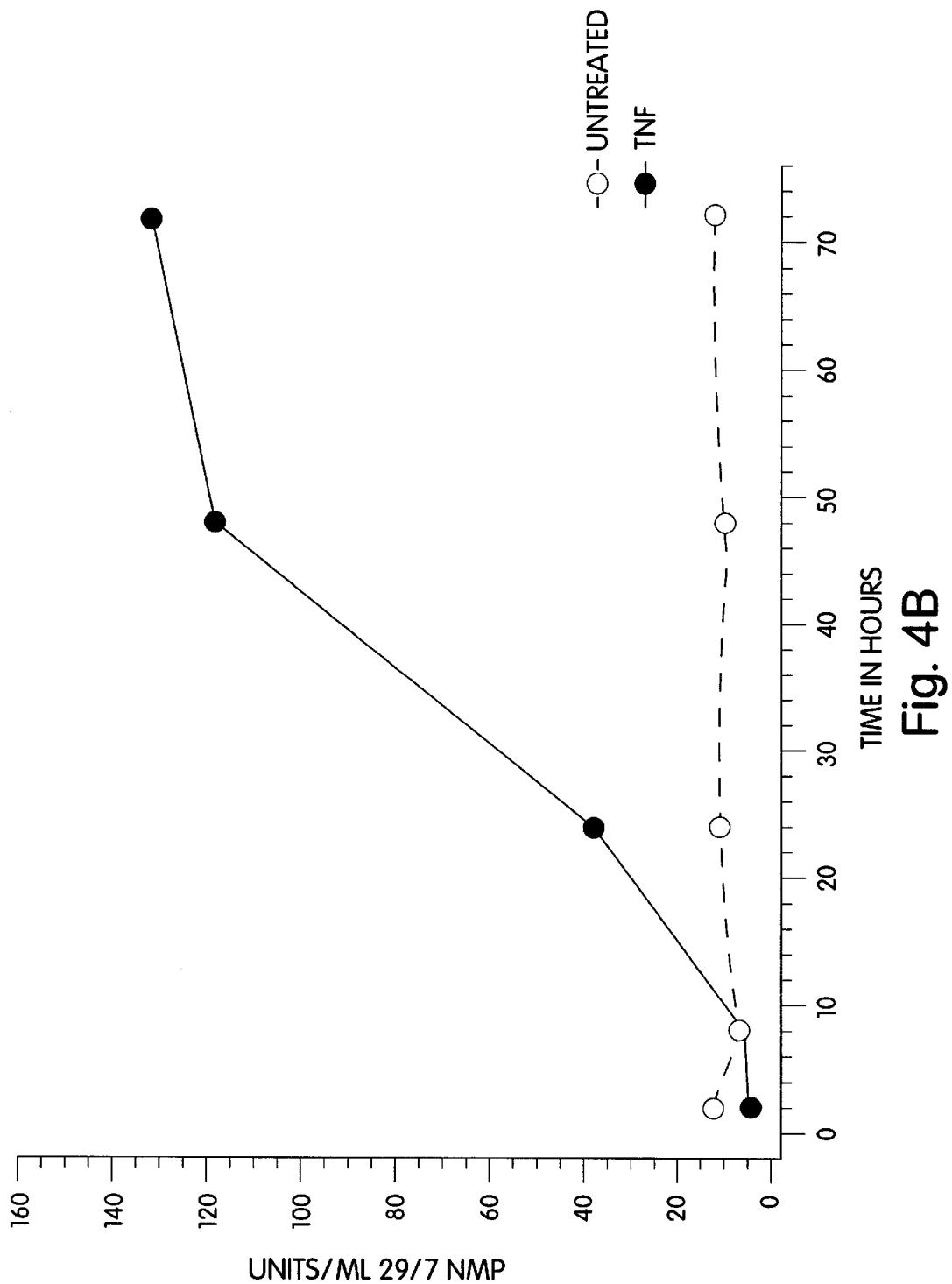

At discrete intervals: 2 hours, 8 hours, 24 hours, 48 hours, and 72 hours, supernatants were removed, spun down at 1200 rpm and frozen at $-80°$ C. Cells remaining adhered were used for slides and PAP-stained (using standard cell staining techniques). Supernatants were assessed by immunoradiometric assay using the 22/18 or 302.29/107.07 ("29/7") antibody combination. As seen in FIG. 4 cell treatment with TNF induces the release of nuclear matrix protein into the supernatant soon after exposure (by 20 hours), whereas the untreated cells do not. FIG. 4A is assayed with the 22/18 combination; FIG. 4B with the 29/7 combination. In addition, histological evaluation of the stained cells verified that the TNF-treated cells showed the characteristics of apoptosis (chromatin condensation, cytoplasmic blebbing).

Dose vs. Density Experiment

Here, MCF7 cells (breast carcinoma, adherent) were grown in a one stage cell factory (Nunc) in DME complete (5% FCS+SerXtend) at $37°$ C. and 5% $CO_2$. These cells then were harvested, resuspended in serum free Minimal Essential Medium contain fungizone and gentamycin (MEM), counted, and seeded into T150 flasks with 35 mls serum free media at different cell densities.

The cells were allowed to die for 7 days at $37°$ C. and 5% $CO_2$. The supernatants were drawn off, spun down at 1000 rpm to remove cell fragments. All supernatants were assayed by immunoradiometric assays using the 22/18, and by the 41/7 antibody combination in an ELISA.

Figure 5:
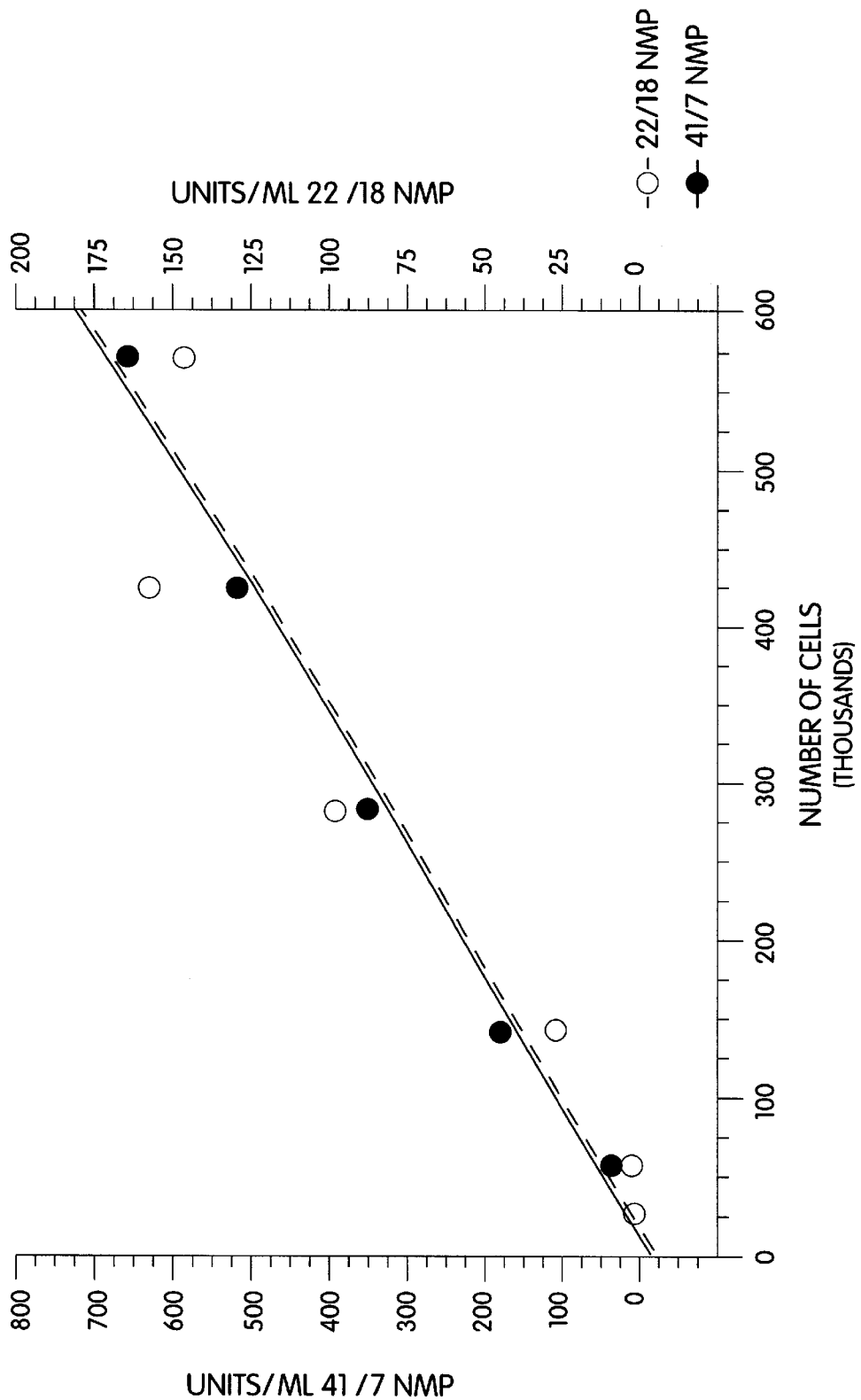
FIG. 5 is a graph correlating nuclear matrix protein release with cell density.

For all nuclear matrix proteins tested, release was essentially directly related to cell density (See FIG. 5). The result is significant as these preliminary data suggest that nuclear matrix protein release is consistent and quantifiable, and values detected can be correlated with cell number.

Cytotoxic Reagent Assay

Figure 6:
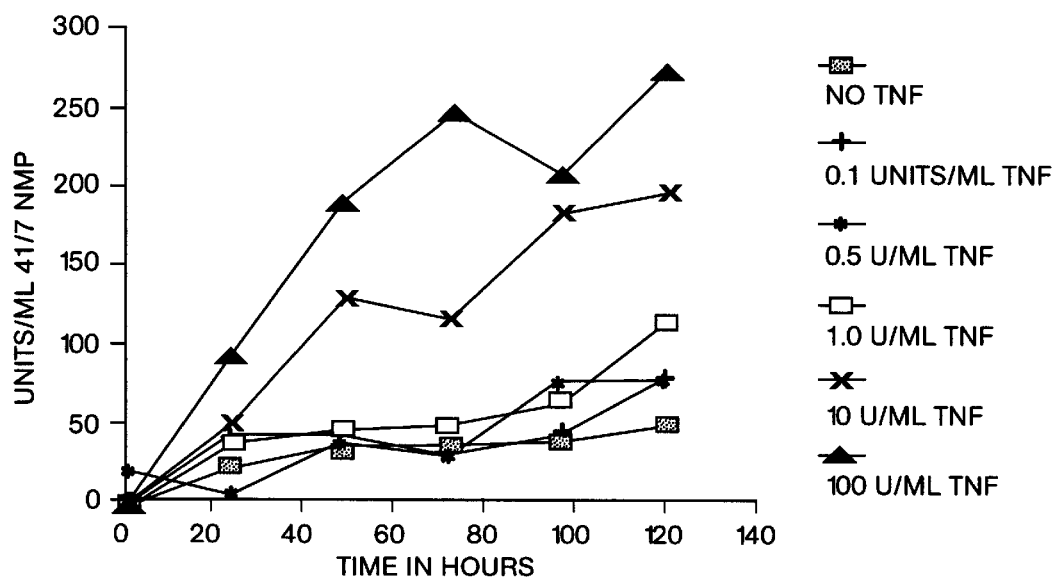
FIG. 6 is a graph correlating TNF dose with the release of soluble nuclear matrix protein detected by the 41/7 antibody combination.

1. In this experiment, the effect of increasing concentrations of TNF on the release of the 41/7 nuclear matrix protein was investigated. MCF7 tissue culture cells growing at $37°$ C. and 5% $CO_2$ in tissue culture medium were exposed to different concentrations of TNF by replacing the tissue culture media with media containing TNF. As shown in FIG. 6, the quantity and rate of release of the 41/7 nuclear matrix protein is related to the dose of TNF added, particularly at doses greater than 1.0 units/ml TNF (FIG. 6).

2. In this experiment, the effect of a known cancer chemotherapeutic agent (Doxorubicin, Sigma Inc.) on soluble nuclear matrix protein release into extracellular fluid was assessed.

A standard curve for live cells was established with MCF7 cells (breast carcinoma, adherent). Cells were seeded into 6 well plates in 2 mls of DME complete (5% FCS+SerXtend) with 0.5 micrograms/ml mitomycin C (Sigma, Inc., Cincinnati) to prevent any cell growth.

After incubating overnight at $37°$ C., 200 $\mu$l of 3-[4, 5 Dimethylthiazol-2-4] 2, 5-dipheny(tetrazoluim bromide), MTT, stock solution (5 mg/ml MTT in phosphate-buffered saline, Sigma, Inc.) were added to each well. After the plates were incubated for four hours at $37°$ C. and 5% $CO_2$ the supernatants were aspirated off and 4 mls of DMSO (dimethyl sulfoxide) were added to solubilize remaining crystals. This was drawn off and the absorbance was read in the spectrophotometer at 562 nm against a blank of straight DMSO.

Cells were treated with Doxorubicin as follows: MCF7 cells were seeded into 6 well plates at a density of $1.3 \times 10^5$ cells/well in 2 mls DME complete. After 72 hours of growth at 37° C. and 5% $CO_2$, the supernatants were aspirated off and replaced with DME complete containing 450 nM Doxorubicin.

At 1, 24, 48, 72, and 96 hours, the supernatants were removed and frozen at −20° C. to assay later. After replacing the supernatant with a fresh 2 ml of DME complete, the number of live cells was determined using the same procedure as for the standard curve. The cell supernatants were assayed by ELISA, using the 41/7 antibody combination. The dose values obtained from these ELISAs were plotted along with standard curve data to observe correlations between the assay measurement of remaining live cells and nuclear matrix protein release (See FIG. 7)

Figure 7:
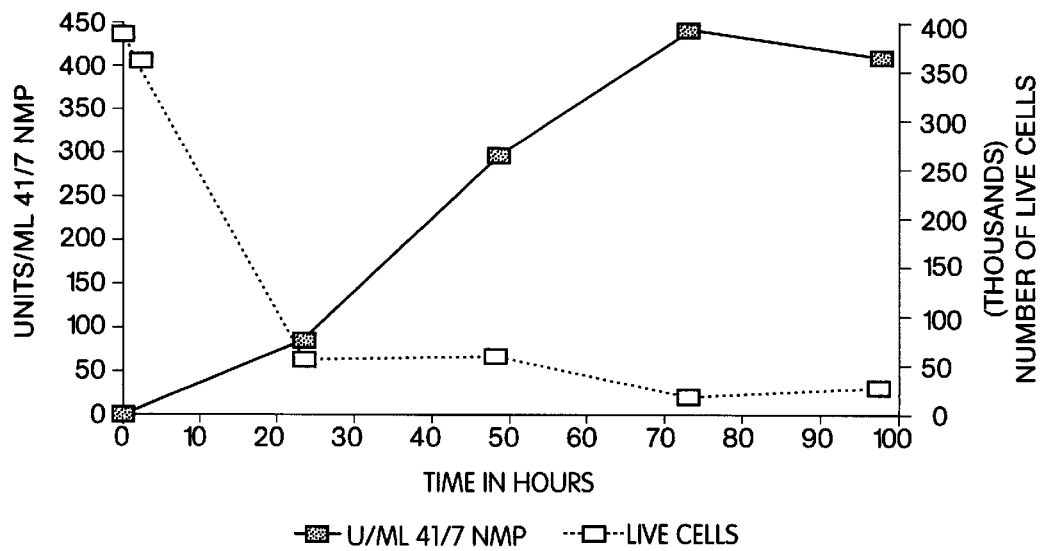
FIG. 7 is a graphic representation of the effect of Doxorubicin on soluble nuclear matrix protein release and cell viability.

As evidenced by FIG. 7, cell viability appears to be inversely related to nuclear matrix protein released.

TNF-Induced Release of Nuclear Matrix Protein

The present invention also may be used to prepare a NM preparation form cells by inducing their release from cells in soluble from with an appropriate agent such as TNF. Generally, a protocol similar to that of the cytotoxic reagent assay may be used to induce protein release. Cells are grown essentially to confluency, and the supernatant then is replaced with DME complete, 250 U/ml TNF. After an appropriate incubation period, the supernatant is drawn off and the soluble nuclear matrix protein extracted from solution by standard protein separation methods, for example, by chromatography on a cationic exchange column or an affinity column, such as an immunoaffinity column. Once purified, the NM preparation may be maintained as a frozen solution until ready to be used. The NM proteins so prepared can be used in immunoassay standards and for the production of further monoclonal and polyclonal antibodies. It is also proposed that these proteins can be used to evaluate their ability to bind to other compounds and thus identify compounds capable of interfering with the nuclear function of particular nuclear matrix proteins. Compounds capable of specifically binding to and interfering with the nuclear function of cancer-specific nuclear matrix proteins, for example, may be useful as cancer chemotherapeutic agents.

The invention may be embodied in other specific forms without departing from the spirit or essential characteristics thereof. The present embodiments are therefore to be considered in all respects as illustrative and not restrictive, the scope of the invention being indicted by the appended claims rather than by the foregoing description, and all changes which come within the meaning and range of equivalency of the claims are therefore intended to be embraced therein.

What is claimed is:

1. A method for evaluating the efficacy of a therapy associated with cell death in a tissue, said method comprising the steps of:

(a) providing first and second fluid samples drawn from a patient after initiation of a said therapy, wherein said first fluid sample is drawn from said patient before said second fluid sample, and wherein at least one of said samples contains soluble debris released from cells of said tissue;

(b) contacting said first and second fluid samples, separately, with a binding partner that binds specifically to a body fluid-soluble interior nuclear matrix protein having a specific binding site for said binding partner;

(c) measuring, in each of said first and second fluid samples, a quantity per unit volume of said body fluid-soluble interior nuclear matrix protein recognized specifically by said binding partner, said quantity being indicative of the magnitude of cell death in said tissue; and (d) comparing said quantities per unit volume of said body fluid-soluble interior nuclear matrix protein in said first and second fluid samples, wherein an increase in said quantity of body fluid-soluble interior nuclear matrix protein in said second fluid sample relative to said first fluid sample is indicative of an increase in cell death and a decrease in said quantity of body fluid-soluble interior nuclear matrix protein in said second fluid sample relative to said first fluid sample is indicative of a decrease in cell death.

2. The method of claim 1 wherein said therapy induces cell death.

3. The method of claim 1, comprising the additional step of, prior to step (a), administering a therapeutic agent or procedure to said patient.

4. The method of claim 3 wherein said therapeutic agent or procedure is a cancer therapeutic agent or procedure.

5. The method of claim 1, wherein said therapy comprises a treatment for a malignancy.

6. The method of claim 5, wherein said malignancy is selected from the group of malignancies consisting of a carcinoma, sarcoma, lymphoma and a myeloma.

7. The method of claim 1 wherein said first and second fluid samples provided in step (a) are selected from the group of samples consisting of blood, serum, plasma, urine, semen, spinal fluid, ascitic fluid, peritoneal fluid, saliva, and sputum.

8. The method of claim 1 wherein said first and second fluid samples are samples of breast exudate.

9. The method of claim 1 wherein said binding partner is an antibody.

10. The method of claim 9 wherein said antibody is a monoclonal antibody.

11. The method of claim 9 wherein said antibody is a polyclonal antibody.

12. The method of claim 1, wherein said first and second fluid samples are urine samples.

13. The method of claim 1, wherein said first and second fluid samples are serum samples.

14. A method for evaluating the efficacy of a therapy associated with cell death in a tissue, said method comprising the steps of:

(a) providing first and second fluid samples from a patient, wherein said first fluid sample is drawn from said patient before administration of said therapy and said second fluid sample is drawn from said patient after administration of said therapy, and wherein at least one of said samples contains soluble debris released from cells of said tissue;

(b) contacting said first and second fluid samples, separately, with a binding partner that binds specifically to a body fluid-soluble interior nuclear matrix protein having a specific binding site for said binding partner;

(c) measuring, in each of said first and second fluid samples, a quantity per unit volume of said body fluid-soluble interior nuclear matrix protein recognized specifically by said binding partner, said quantity being indicative of the magnitude of cell death in said tissue; and (d) comparing said quantities per unit volume of said body fluid-soluble interior nuclear matrix protein in said first and second fluid samples, wherein an increase in said quantity of body fluid-soluble interior nuclear matrix protein in said second fluid sample relative to said first fluid sample is indicative of an increase in cell death and a decrease in said quantity of body fluid-soluble interior nuclear matrix protein in said second fluid sample relative to said first fluid sample is indicative of a decrease in cell death.

15. The method of claim 14, comprising the additional step of administering a therapeutic agent or procedure to said patient.

16. The method of claim 15, wherein said therapeutic agent or procedure is a cancer therapeutic agent or procedure.

17. The method of claim 14, wherein said therapy comprises a treatment for a malignancy.

18. The method of claim 17, wherein said malignancy is selected from the group of malignancies consisting of a carcinoma, sarcoma, lymphoma and a myeloma.

19. The method of claim 14, wherein said first and second fluid samples provided in step (a) are selected from the group of samples consisting of blood, serum, plasma, urine, semen, spinal fluid, ascitic fluid, peritoneal fluid, saliva, and sputum.

20. The method of claim 14, wherein said first and second fluid samples are samples of breast exudate.

21. The method of claim 14, wherein said binding partner is an antibody.

22. The method of claim 21, wherein said antibody is a monoclonal antibody.

23. The method of claim 21, wherein said antibody is a polyclonal antibody.

24. The method of claim 14, wherein said first and second fluid samples are urine samples.

25. The method of claim 14, wherein said first and second fluid samples are serum samples.

* * * * *